United States Patent [19]

Muranaka

[11] Patent Number: 4,791,480
[45] Date of Patent: Dec. 13, 1988

[54] ENDOSCOPIC SYSTEM WITH ADJUSTABLE LIGHT SOURCE

[75] Inventor: Yuuichi Muranaka, Ootawara, Japan

[73] Assignee: Kabushiki Kaisha Toshiba, Kawasaki, Japan

[21] Appl. No.: 95,267

[22] Filed: Sep. 11, 1987

[30] Foreign Application Priority Data

Sep. 29, 1986 [JP] Japan .................... 61-228230

[51] Int. Cl.⁴ .................... H04N 7/18; A61B 1/06
[52] U.S. Cl. .................... 358/98; 358/228; 128/6
[58] Field of Search .................... 358/98, 228; 128/4–6

[56] References Cited

U.S. PATENT DOCUMENTS 4,625,714 12/1986 Toyota et al. .................... 358/98 X
4,646,724 3/1987 Sato et al. .................... 128/6
4,704,520 11/1987 Kanno et al. .................... 128/6 X Primary Examiner—Howard W. Britton
Assistant Examiner—Victor R. Kostak
Attorney, Agent, or Firm—Foley & Lardner, Schwartz, Jeffery, Schwaab, Mack, Blumenthal & Evans

[57] ABSTRACT

An endoscopic system comprises a light source for continuously irradiating an object to be photographed; a solid-state camera element for obtaining image signals from the object; a memory for storing a predetermined unit of the image signals obtained from the solid-state camera element; a display converting device for reading out a unit image under a freezing state from the memory; and a intercepting device for intercepting continuous light of the light source when the display converting device reads out a frozen unit image from the memory, such that pulsed light is irradiated onto the object in synchronous with a timing of transferring a unit image from the solid-state camera element.

7 Claims, 5 Drawing Sheets

ENDOSCOPIC SYSTEM WITH ADJUSTABLE LIGHT SOURCE

BACKGROUND OF THE INVENTION

1. Field of the Invention

The present invention relates to an endoscopic system adopting a solid-state camera element, and particularly to an endoscopic system which can provide excellent real-time images and frozen images.

2. Description of the Prior Art

Conventionally, in a kind of endoscopic system, an object to be photographed is irradiated by continuous light or by pulsed light to obtain real-time images or frozen images of the object, respectively.

If the object is irradiated by the continuous light to obtain a frozen image thereof, a blur may be caused in the obtained frozen image. Therefore, the pulsed light is usually used for obtaining a frozen image having no blur. As shown in FIG. 1, the pulsed light is irradiated onto the object in synchronism with the field shift timing of a solid-state camera element. Electric charge of the solid-state camera element is transferred at the timing of, for instance, a 1/60 second interval corresponding to a field shifting rate shown in FIG. 1. In synchronizing with the intervals of respective fields A, B, C, D, E, F, and so on to be shifted, the pulsed light is emitted repeatedly.

When pulsed light of type "A" shown in FIG. 1 is used to obtain real-time images, the obtained images may be continuous with 1/60 second intervals and not intermittent. However, when the pulsed light of type "A" is used to obtain a frozen image, the image will not successfully be frozen because there is a time difference of 1/60 second between an image of the field "A" and an image of the field "B". When pulsed light of type "B" shown in FIG. 1 is used, a good frozen image of one frame may be obtained, but good real-time images may not be obtained with the same pulsed light of type "B". This is because a time difference between an image of the field "D" and an image of the field "E" is "L" which is larger than 1/60 second to deteriorate continuity in the real-time images. Namely, when the real-time images by the light of type "B" are displayed on a monitoring display screen such as a CRT, the images will not be continuous but intermittent.

As described in the above, the continuous light irradiation will cause a blur in a frozen image, and the pulsed light irradiation will cause problems that a frozen image of a frame may not successfully be obtained from a quickly moving object and that real time images on a monitoring display screen such as a CRT are not continuous but intermittent. Therefore, it causes an unnatural feeling to an operator who is monitoring the images.

SUMMARY OF THE INVENTION

In view of the above, an object of the present invention is to provide an endoscopic system adopting a solid-state camera element, which does not deteriorate a frozen image and can improve continuity in real-time images.

A feature of the present invention resides in an endoscopic system comprising a light source for continuously emitting light; a display converting means for optionally freezing frame images to be generated according to image signals from a solid-state camera element; a light source intercepting means for intercepting the continuous light of the light source, the light source intercepting means responding only to a freezing instruction sent thereto from the display converting means so as to irradiate an object to be photographed with pulsed light in synchronism with a field or frame transfer timing of the solid-state camera element; and an image adjusting means for adjusiing an irradiation quantity of the light source such that a frozen image having a brightness equal to that of a real-time image is obtained for every intercepting operation of the light source intercepting means.

According to the endoscopic system of the present invention, the light source is arranged to emit light continuously, the solid-state camera element is constructed to photograph the object and continuously provides image signals thereof, and the display converting means is constructed to store the image signals into a frame memory and optionally freeze the frame image data stored in the frame memory.

When the display converting means sends a freezing instruction to the light source intercepting means, the light source intercepting means intercepts the continuous light of the light source, thereby providing pulsed light synchronizing with a frame or field transfer timing of the solid-state camera element. However, without having the freezing instruction, the light source intercepting means will never intercept the continuous light of the light source.

The image adjusting means adjusts an irradiation quantity of the light source such that a frozen image having a brightness equal to that of a real-time image is realized on the display screen for every intercepting operation of the light source intercepting means.

Therefore, when real-time images are displayed on the display screen, light from the light source continuously irradiates the object so that the real-time images based on frame image data stored by the display converting means into the frame memory will be continuous to completely eliminate the unnatural intermittence.

When a frozen image is displayed on the display screen, light from the light source is intercepted and released repeatedly by the light source intercepting means to obtain pulsed light, and a quantity of the pulsed light is adjusted to a predetermined value by the image adjusting means. Therefore, the frozen image will have the same brightness as that of the real-time image and thus avoid the quality of the frozen image from being deteriorated.

BRIEF DESCRIPTION OF THE DRAWINGS

These and other objects, features and advantages of the present invention will become apparent from the following descriptions of preferred embodiments taken in conjunction with the accompanying drawings in which.

DETAILED DESCRIPTION OF THE EMBODIMENTS

Figure 1:
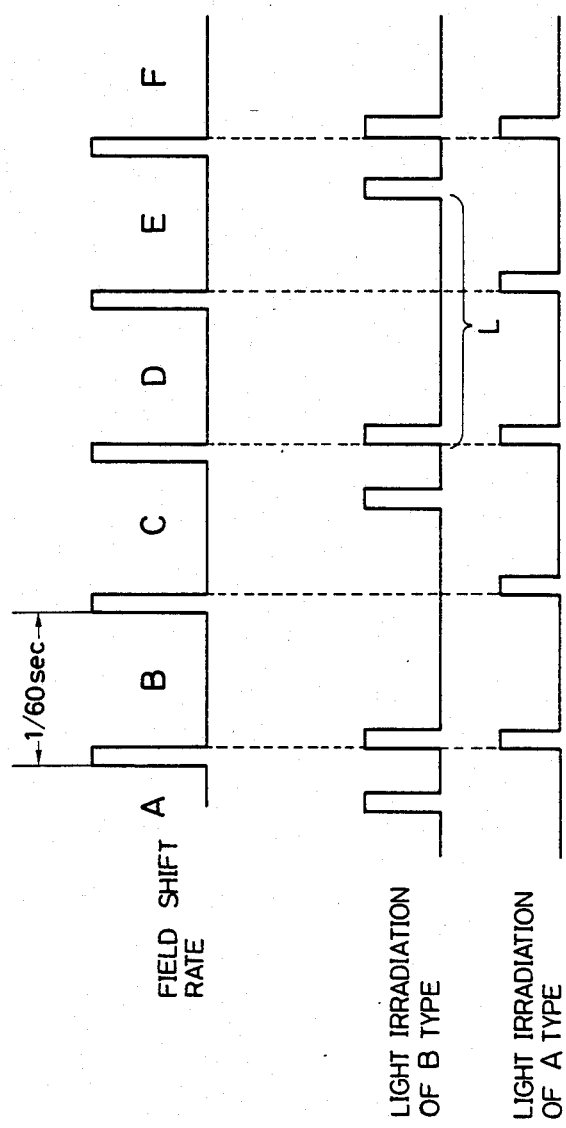
FIG. 1 is a time chart showing the relationship between a field shift rate and irradiated light in an endoscopic system according to a prior art.
Figure 2:
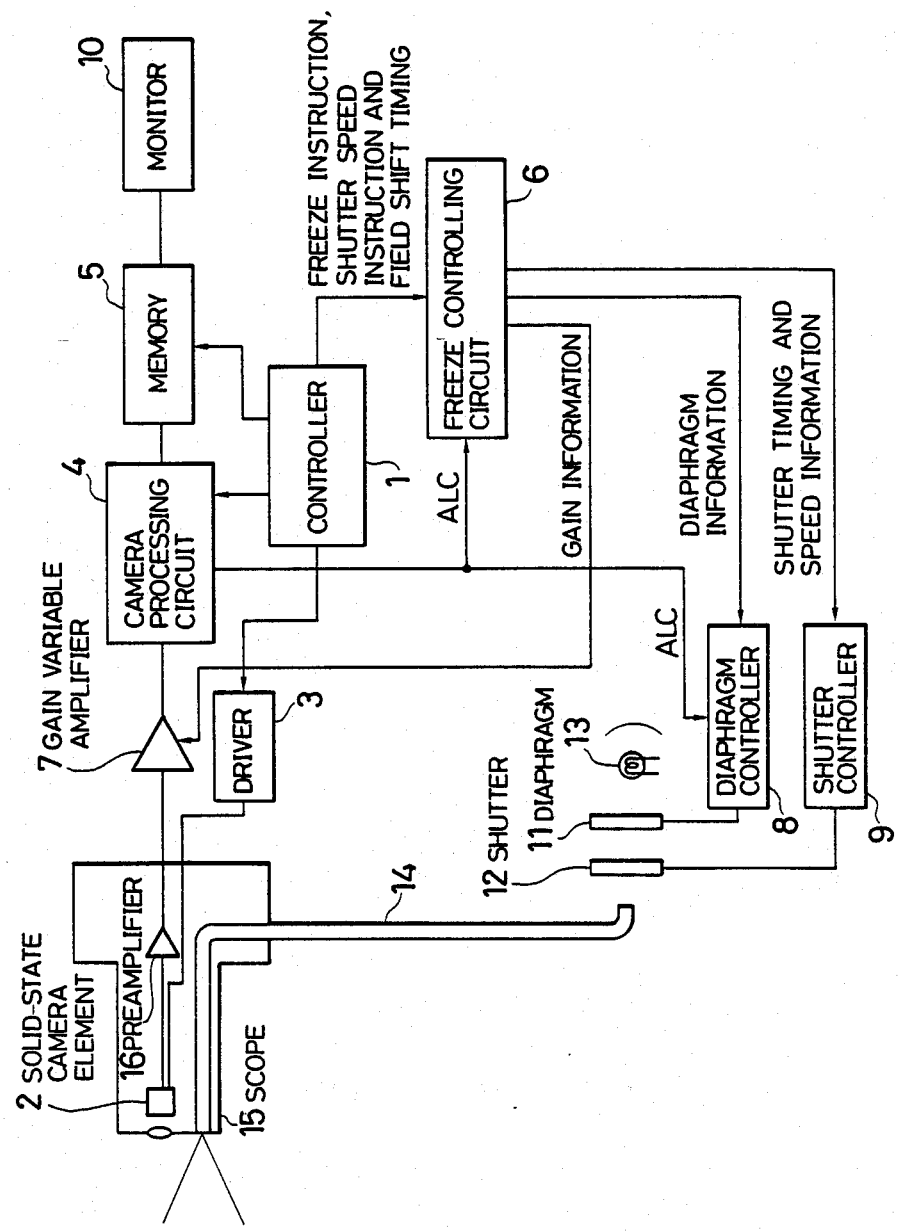
FIG. 2 is a block diagram showing the constitution of an electronic endoscopic system according to an embodiment of the present invention.

FIG. 2 is a view showing an electronic endoscopic system embodying the present invention.

In the electronic endoscopic system of this embodiment, a controller 1 is disposed as a control center which controls a driver 3 for driving a solid-state camera element 2, a camera processing circuit 4, a frame memory 5, and a freeze controlling circuit 6.

The controller 1 controls the frame memory 5 such that a frame image is read under a freezing state from the frame memory 5 in response to a freezing input operation. The controller 1 also supplies controlling signals such as a freezing instruction, a shutter speed instruction, and a field shift timing.

The freeze controlling circuit 6 receives the freezing instruction, the shutter speed instruction and the field shift timing from the controller 1, as well as receiving an automatic light quantity controlling signal (ALC signal) from the camera processing circuit 4. Thereby, the freeze controlling circuit supplies gain information to a gain variable amplifier 7, diaphragming information to a diaphragm controller 8, and shutter timing and speed information to a shutter controller 9.

The camera processing circuit 4 also supplies the ALC signal to the diaphragm controller 8. The frame memory 5 sends image data to a monitor 10.

The diaphragm controller 8 controls a diaphragm 11, and the shutter controller 9 controls a shutter 12. Continuous light from a light source 13 is transferred through a light guide 14 to an endoscope 15.

The endoscope 15 comprises the above-mentioned solid-state camera element 2 and a preamplifier 16 for preamplifying image signals transmitted from the solid-state camera element 2.

According to this embodiment, the controller 1 and the freeze controlling circuit 6 constitute a display converting means, the shutter 12 and the shutter controller 9 constituting a light source intercepting means, and the gain variable amplifier 7, the diaphragm 11 and the diaphragm controller 8 constituting an image adjusting means.

The operation of the electronic endoscopic system according to the embodiment with the above-mentioned arrangement will be described.

Under a normal state to obtain real-time images, the diaphragm controller 8 controls the diaphragm 11 in response to the ALC signal from the camera processing circuit 4. Under this normal state, the freeze controlling circuit 6 does not send control information to the gain variable amplifier 7 and to the shutter controller 9 so that the gain variable amplifier 7 is maintained at a constant state, and the shutter 12 is left open. Therefore, under normal state, the continuous light from the light source 13 is directly transferred to an object to be photographed.

Figure 3:
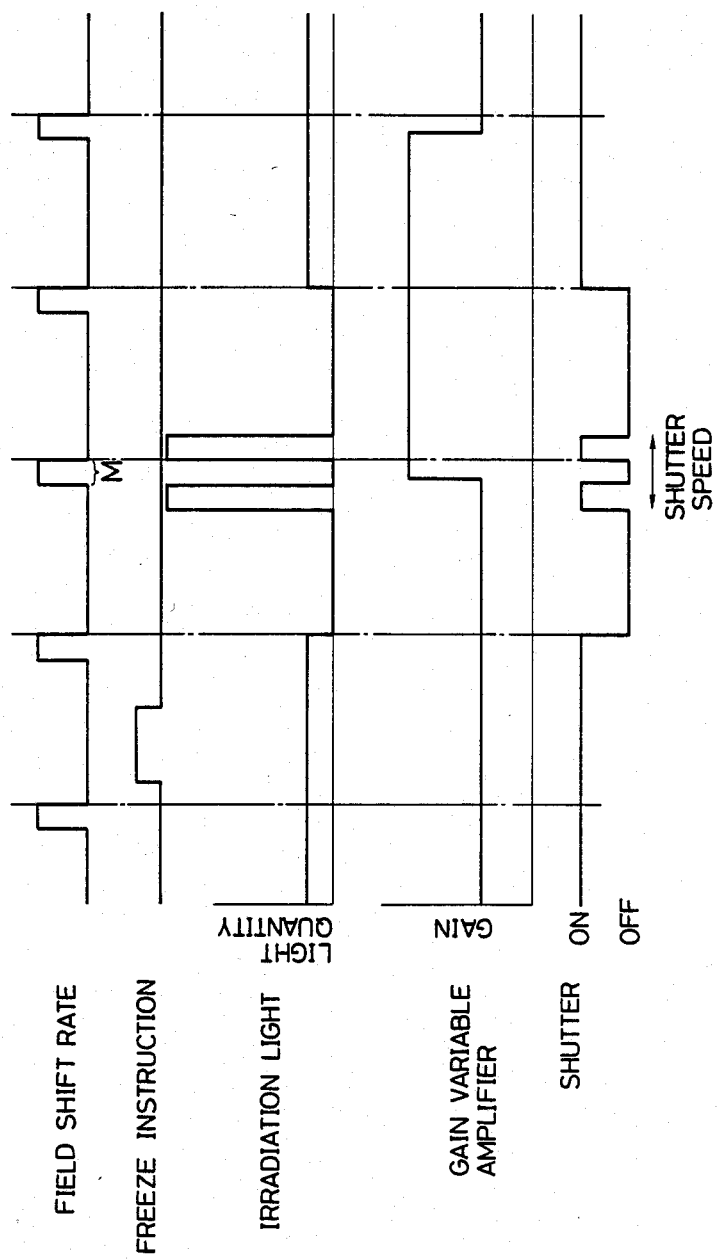
FIG. 3 is a time chart showing waveforms of various elements in a freezing operation according to the embodiment shown in FIG. 2.

In a freezing state in which an freezing instruction is generated by the controller 1 in response to a predetermined input operation, the respective elements are operated as shown in the time chart of FIG. 3.

When the freezing instruction is generated in the middle of a repeating cycle of field shifting, the freeze controlling circuit 6 receives the freezing instruction and sends an instruction for temporarily closing the shutter 12 to the shutter controller 9 in synchronous with the field shift timing, thus closing the shutter 12.

At this time, the freeze controlling circuit 6 prepares diaphragm information on the basis of the ALC signal from the camera processing circuit 4 and a value of the shutter speed instruction from the controller 1, and outputs the diaphragm information to the diaphragm controller 8 such that the same ALC signal as that for the real-time image is generated out of the camera processing circuit 4. At this time, if a light quantity is not sufficient with the diaphragm being fully opened, the freeze controlling circuit 6 provides gain information to increase a gain of the gain variable amplifier 7.

At the same time, synchronizing with the next field shift timing, the freeze controlling circuit 6 sends an instruction to the shutter controller 9 such that one light pulse is generated in each of adjacent two fields in a shortest interval extending over the same adjacent two fields, and, with a shutter speed corresponding to this instruction, the shutter controller 9 opens and closes the shutter 12 two times.

At the next field shift timing following the two times of open and close of the shutter 12, the freeze controlling circuit 6 provides an instruction for opening the shutter 12 to the shutter controller 9.

As shown in FIG. 3, the shutter 12 is controlled to be closed during a field shifting period "M". This is done to avoid light from irradiating the object, thereby equalizing the light quantities of the two field periods to each other.

In this case, it is preferable to make a closing time period of the shutter 12 longer than the filed shift period "M".

Only when the controller 1 generates the freezing instruction, the freeze controlling circuit 6 generates controlling information for controlling and operating the diaphragm controller 8, the gain variable amplifier 7 and the shutter controller 9, as indicated by the time chart of FIG. 3. Therefore, a frame image read out under the freezing state from the frame memory 5 may never be influenced by the continuous irradiation which will cause a blur in the frozen image. Further, an output of the gain variable amplifier 7 under the freezing state will have the same brightness as that for a real-time state and be applied to the camera processing circuit 4 so that a frozen image having the same brightness as that of a real-time image can be obtained.

As mentioned in the above, according to the electronic endoscopic system of this embodiment under the real-time state, image signals from the solid-state camera element 2 are stored in the frame memory 5 through the preamplifier 16, the gain variable amplifier 7 and the camera processing circuit 4, and, according to the image data stored in the frame memory 5, real time images are displayed on the monitor 10. These real time images have improved continuity and never give the unnatural intermittence.

While diagnosing and treating a patient by observing good real-time images, a physician may change the real-time images to a frozen image to perform a further objective diagnosis and to see a treatihg progress of the patient. In this case, as described with reference to the time chart shown in FIG. 3, the influence of the continuous light irradiation which will cause a blur in the frozen image is completely eliminated, and the light irradiation is controlled such that a brightness of the frozen image is the same as that of the real-time images, thus providing a clear frozen image.

Since two light pulses are generated in two adjacent fields respectively within a shortest interval extending over the same two adjacent fields, a blur generated while storing image signals of a moving object is minimized as much as possible to obtain a clear frozen image of one frame.

According to the above-mentioned embodiment, it is possible to irradiate a light pulse onto the object for every period corresponding to a starting edge of a field by providing an instruction from the controller 1 to the freeze controlling circuit 6. In this case, if an object moves, a flicker may be caused in an image due to a temporal shift between a first field and a second field. However, a frozen image of the first field may be obtained without a blur.

Although the above-mentioned embodiment has used a monochrome solid-state camera element, the present invention is applicable for a color television type endoscopic system in which three primary colors such as red (R), green (G) and blue (B) are successively irradiated onto an object to store image signals corresponding to the respective colors from the solid-state camera element into respective memories, and color image signals are obtained by synthesizing output signals of the respective memories.

Figure 4:
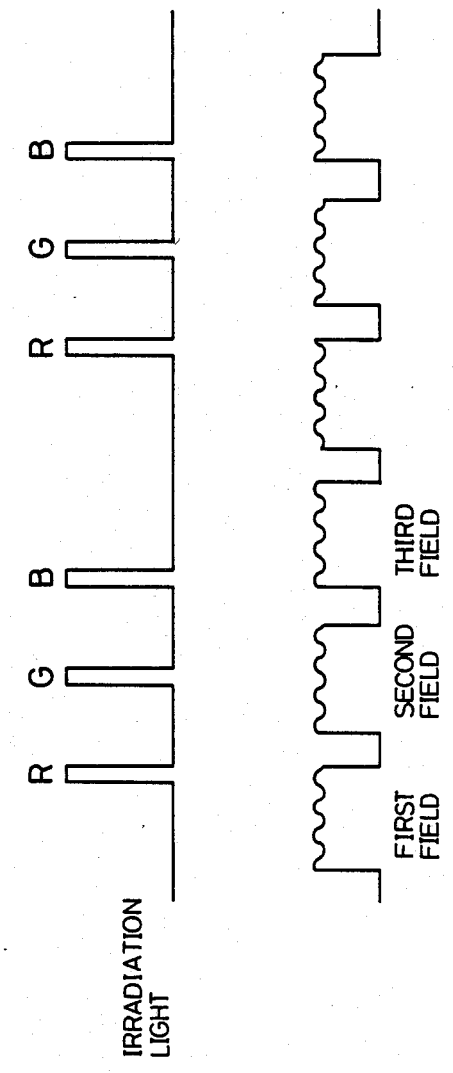
FIG. 4 is a time chart partly showing waveforms in operation according to another embodiment of the present invention.

When the present invention is applied for the color endoscopic system, the components of the first embodiment explained with reference to the FIGS. 2 and 3 are also used for the color system. As shown in FIG. 4, a red (R) light is controlled to be generated at a trailing end of a first field, a green (G) light at an optional point in a second field, and a blue (B) light at a leading end of a third field. Namely, the light pulses are emitted in a shortest period extending over the three fields so that a blur and a color breakup are remarkably reduced to provide a clear frozen image.

Figure 5:
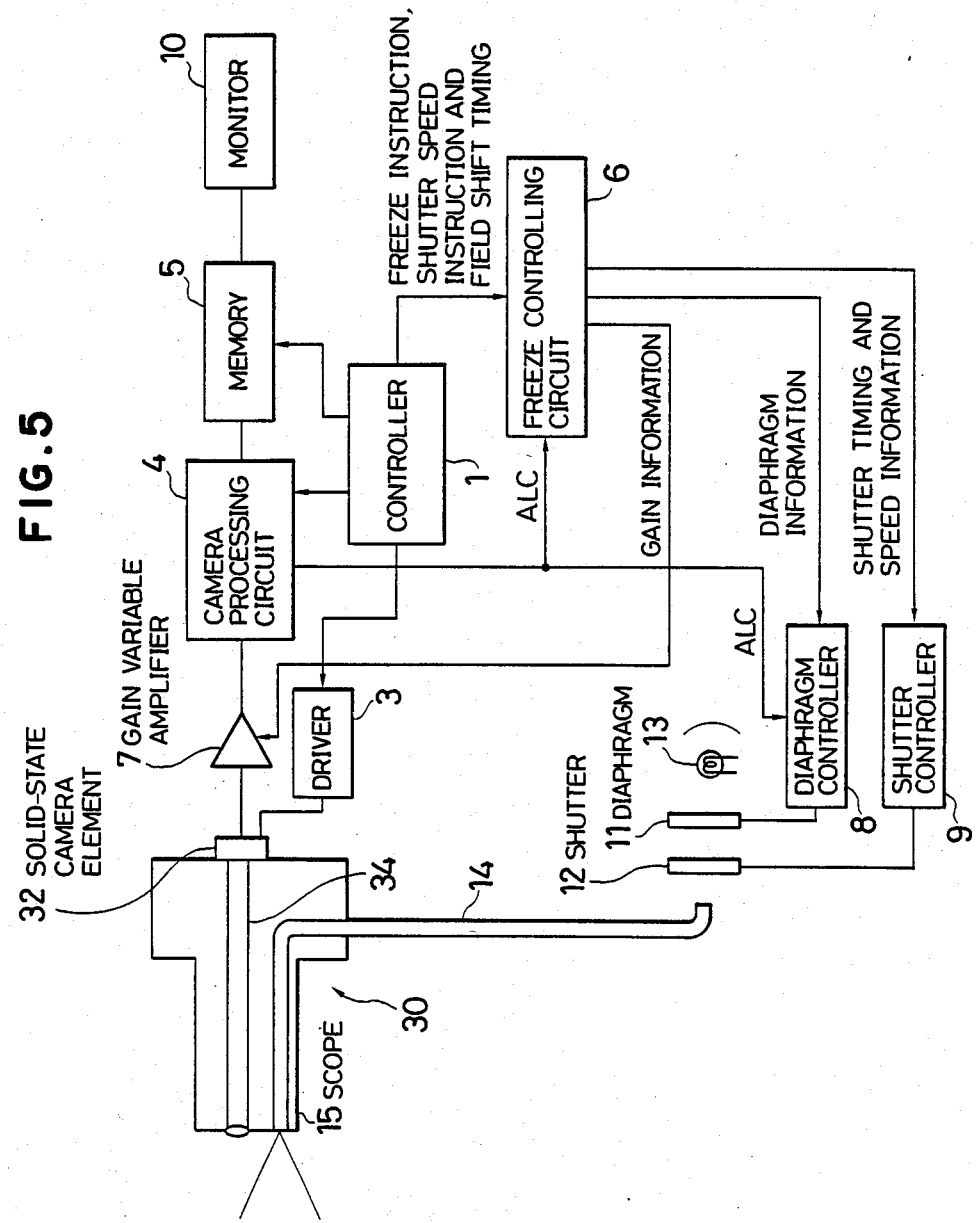
FIG. 5 is a block diagram showing a fiber scope according to the present invention.

Although the present invention has been applied for the electronic endoscopic system as shown in FIG. 2, the present invention is applicable for a fiber scope as shown in FIG. 5. In the figure, a fiber scope 30 is provided with a solid-state camera element 32 which is spaced apart from an object. There is disposed an image guide fiber 34 for guiding an image of the object to the solid-state camera element 32. Other constitution of this embodiment is the same as that of the first embodiment shown in FIG. 2 so that an explanation thereof will be omitted.

In summary, an electronic endoscopic system according to the present invention irradiates an object with continuous light in a normal state to display real-time images so that the continuity of the obtained real-time images may remarkably be improved with no unnatural intermittence. Further, the endoscopic system of the present invention controls a freezing state to eliminate a blur from a frozen image and secure for the frozen image the ame brightness as that of the real-time image so that a clear frozen image can be obtained.

Various modifications will become possible for those skilled in the art after reviewing the teachings of the present disclosure without departing from the scope thereof.

What is claimed is:
1. An endoscopic system comprising:
(a) a light source for continuously irradiating with light an object to be photographed;
(b) a solid-state camera element for obtaining image signals from the object;
(c) a memory for storing the image signals obtained from said solid-state camera element as predetermined units;
(d) display converting means for reading out a unit image corresponding to one of the predetermined units under a freezing state from said memory;
(e) intercepting means for intercepting the continuous light from said light source when said display converting means reads units of the frozen image from said memory, such that pulsed light is irradiated onto said object in synchronism with the transferring the image signal corresponding to one of the units from said solid-state camera element; and
(f) image adjusting means for adjusting a quantity of light irradiated from said light source such that a frozen image has substantially the same brightness as that of a real-time image for every light intercepting operation of said light intercepting means.

2. The endoscopic system as claimed in claim 1, wherein each of the units corresponds to a frame of an image.

3. The endoscopic system as claimed in claim 1 wherein said light intercepting means comprises a shutter for intercepting light from said light source to be irradiated onto said object, and a shutter controller for controlling said shutter according to a freezing instruction from said display converting means.

4. The endoscopic system as claimed in claim 1, wherein said image adjusting means comprises a diaphragm for adjusting a quantity of light irradiated from said light source onto said object, and a diaphragm controller for adusting said diaphragm according to a freeze instruction signal from said display converting means.

5. An endoscopic system comprising:
(a) a light source for continuously irradiating with light an object to be photographed;
(b) a solid-state camera element for obtaining image signals form the object;
(c) a memory for storing the image signals obtained from said solid-state camera element, as predetermined units;
(d) display converting means for reading out a unit image corresponding to one of the predetermined units under a freezing state from said memory;
(e) interecepting means for intercepting the continuous light from said light source when said display converting means reads out a unit of frozen image from said memory, such that pulsed light is irradiated onto said object in synchronism with the transfer of an image signal corresponding to one of the units from said solid-state camera element; and
(f) image adjusting means for adjusting a quantity of light irradiated from said light source such that a frozen image has substantially the same brightness as that of a real-time image for every light intercepting operation of said light intercepting means, said image adjusting means comprising a diaphragm for adjusting a quantity of light irradiated from said light source onto said object, a diaphragm controller for adjusting said diaphragm according to a freeze instruction signal from said display converting means, and a gain variable amplifier for adjusting a gain of an image signal from said solid-state camera element according to a freeze instruction signal from said display converting means.

6. An endoscopic system comprising:

(a) a light source for continuously irradiating with light an object to be photographed;
(b) a solid-state camera element for obtaining image signals from the object;
(c) a memory for storing as predetermined units the image signals obtained from said solid-state camera element;
(d) display converting means for reading out a unit image corresponding to one of the predetermined units under a freezing state from said memory;
(e) intercepting means for intercepting the continuous light from said light source when said display converting means reads out a unit of a frozen image from said memory, such that pulsed light is irradiated onto said object in synchronism with the transfer of an image signal corresponding to one of the units from said solid-state camera element; and
(f) image adjusting means for adjusting a quantity of light irradiated from said light source such that a frozen image has substantially the same brightness as that of a real-time image for every light intercepting operation of said light intercepting means, said light intercepting means comprising a shutter for intercepting light of said light source to be irradiated onto said object, and a shutter controller for controlling said shutter according to a freezing instruction from said display converting means, said shutter controller being constructed to control said shutter such that two light pulses are generated in two adjacent frames respectively within the shortest interval between said two adjacent frames.

7. An endoscopic system comprising:
(a) a light source for continuously irradiating with light an object to be photographed;
(b) a solid-state camera element for obtaining image signals from the object;
(c) a memory for storing as predetermined units the image signals obtained from said solid-state camera element;
(d) display converting means for reading out a unit image corresponding to one of the predetermined units under a freezing state from said memory;
(e) intercepting means for intercepting the continuous light from said light sources when said display converting means reads out a unit of frozen image from said memory, such that pulsed light is irradiated onto said object in synchronism with the transfer of the image signal corresponding to one of the units from said solid-state camera element; and
(f) image adjusting means for adjusting a quantity of light irradiated from said light source such that a frozen image has substantially the same brightness as that of a real-time image for every light intercepting operation of said light intercepting means, said light intercepting means comprising a shutter for intercepting light of said light source to be irradiated onto said object, and a shutter controller for controlling said shutter according to a freezing instruction from said display converting means;
said display onverting means comprising;
a controller for controlling said memory such that a frame image under a freezing state is read out from said memory in response to a predetermined freezing operation, and further supplying controlling signals including a freezing instruction, a shutter speed instruction, and a field shift timing, and
a freeze controlling circuit for receiving said freezing instruction, shutter speed instruction and field shift timing from said controller to send the shutter timing and speed information to said shutter controller.

* * * * *